(12) United States Patent
Jacobsen et al.

(10) Patent No.: US 8,717,428 B2
(45) Date of Patent: May 6, 2014

(54) LIGHT DIFFUSION APPARATUS

(75) Inventors: Stephen C. Jacobsen, Salt Lake City, UT (US); David P. Marceau, Salt Lake City, UT (US)

(73) Assignee: Raytheon Company, Waltham, MA (US)

( * ) Notice: Subject to any disclaimer, the term of this patent is extended or adjusted under 35 U.S.C. 154(b) by 604 days.

(21) Appl. No.: 12/896,743

(22) Filed: Oct. 1, 2010

(65) Prior Publication Data

US 2011/0242302 A1 Oct. 6, 2011

Related U.S. Application Data

(60) Provisional application No. 61/247,892, filed on Oct. 1, 2009.

(51) Int. Cl.
| | |
|---|---|
| *A61B 1/04* | (2006.01) |
| *G02B 5/02* | (2006.01) |
| *G02B 26/00* | (2006.01) |
| *G02B 26/02* | (2006.01) |
| *G02F 1/1335* | (2006.01) |

(52) U.S. Cl.
CPC .......... *G02F 1/133606* (2013.01); *G02F 2001/133607* (2013.01); *G02F 1/133504* (2013.01)
USPC ............ 348/68; 359/599; 359/296; 359/228; 359/227

(58) Field of Classification Search
CPC ............ G02F 1/133606; G02F 1/133504
USPC ............ 348/68; 359/599; 356/241.1–6, 356/445–448
See application file for complete search history.

(56) References Cited

U.S. PATENT DOCUMENTS

| | | | |
|---|---|---|---|
| 3,817,635 | A | 6/1974 | Kawahar |
| 3,856,000 | A | 12/1974 | Chikama |
| 3,886,933 | A | 6/1975 | Mori et al. |
| 3,918,438 | A | 11/1975 | Hayamizu et al. |
| 3,971,065 | A | 7/1976 | Bayer |
| 4,277,168 | A | 7/1981 | Oku |
| 4,283,115 | A | 8/1981 | Fraissl |
| 4,349,456 | A * | 9/1982 | Sowman ............ 428/402 |

(Continued)

FOREIGN PATENT DOCUMENTS

| | | |
|---|---|---|
| CN | 1481753 | 3/2004 |
| DE | 197 42 973 | 4/1998 |

(Continued)

OTHER PUBLICATIONS

Obreja et al., Poly (vinyl-alcohol) Films for Microphotonics, 2004, IEEE, pp. 1-4.*

(Continued)

*Primary Examiner* — Sath V Perungavoor
*Assistant Examiner* — Peter D Le
(74) *Attorney, Agent, or Firm* — Thorpe North & Western LLP (57) ABSTRACT

A light diffusing composition that optimizes image clarity from a SSID comprising a translucent matrix further comprising a plurality of hollow micro-particles. The plurality of hollow micro-particles are dispersed throughout the translucent matrix and a fluid is disposed within the hollow micro-particle. A refractive index of the fluid within the hollow micro-particle is different than a refractive index of the translucent matrix.

22 Claims, 7 Drawing Sheets

(56) References Cited

U.S. PATENT DOCUMENTS

| | | | |
|---|---|---|---|
| 4,360,275 A * | 11/1982 | Louderback | 356/446 |
| 4,403,985 A | 9/1983 | Boretos | |
| 4,475,902 A | 10/1984 | Schubert | |
| 4,487,206 A | 12/1984 | Aagard | |
| 4,491,865 A | 1/1985 | Danna et al. | |
| 4,515,444 A | 5/1985 | Prescott et al. | |
| 4,573,450 A | 3/1986 | Arakawa | |
| 4,585,349 A | 4/1986 | Gross et al. | |
| 4,588,294 A | 5/1986 | Siegmund | |
| 4,589,404 A * | 5/1986 | Barath et al. | 600/108 |
| 4,593,313 A | 6/1986 | Nagasaki et al. | |
| 4,594,613 A | 6/1986 | Shinbori et al. | |
| 4,600,831 A | 7/1986 | Hutley | |
| 4,604,992 A | 8/1986 | Sato | |
| 4,620,534 A | 11/1986 | Zartman | |
| 4,621,284 A | 11/1986 | Nishioka et al. | |
| 4,622,954 A | 11/1986 | Arakawa et al. | |
| 4,626,079 A | 12/1986 | Nakamura et al. | |
| 4,641,927 A | 2/1987 | Prescott et al. | |
| 4,646,724 A | 3/1987 | Sato et al. | |
| 4,672,218 A * | 6/1987 | Chrisman et al. | 250/574 |
| 4,706,118 A | 11/1987 | Kato et al. | |
| 4,707,134 A * | 11/1987 | McLachlan et al. | 356/342 |
| 4,723,843 A | 2/1988 | Zobel | |
| 4,725,721 A | 2/1988 | Nakamura | |
| 4,745,470 A | 5/1988 | Yabe et al. | |
| 4,745,471 A | 5/1988 | Takamura et al. | |
| 4,783,591 A | 11/1988 | Sullivan | |
| 4,785,815 A | 11/1988 | Cohen | |
| 4,790,624 A | 12/1988 | Van Hoye et al. | |
| 4,791,479 A | 12/1988 | Ogiu et al. | |
| 4,802,487 A | 2/1989 | Martin et al. | |
| 4,803,562 A | 2/1989 | Eino | |
| 4,832,003 A | 5/1989 | Yabe | |
| 4,843,416 A | 6/1989 | Brower | |
| 4,846,785 A | 7/1989 | Cassou et al. | |
| 4,859,040 A | 8/1989 | Kitagishi et al. | |
| 4,867,137 A | 9/1989 | Takahashi | |
| 4,867,138 A | 9/1989 | Kubota et al. | |
| 4,867,174 A | 9/1989 | Skribiski | |
| 4,880,298 A | 11/1989 | Takada | |
| 4,895,138 A | 1/1990 | Yabe | |
| 4,916,534 A | 4/1990 | Takhashi et al. | |
| 4,926,257 A | 5/1990 | Miyazaki | |
| 4,930,880 A | 6/1990 | Miyauchi | |
| 4,932,394 A | 6/1990 | Nanaumi | |
| 4,934,340 A | 6/1990 | Ebling et al. | |
| 4,941,457 A | 7/1990 | Hasegawa | |
| 4,998,807 A | 3/1991 | Uzawa et al. | |
| 5,006,928 A | 4/1991 | Kawajiri et al. | |
| 5,009,483 A | 4/1991 | Rockwell, III | |
| 5,021,888 A | 6/1991 | Kondou et al. | |
| 5,022,972 A * | 6/1991 | David et al. | 204/549 |
| 5,032,913 A | 7/1991 | Hattori et al. | |
| 5,040,069 A | 8/1991 | Matsumoto et al. | |
| 5,061,036 A | 10/1991 | Gordon | |
| 5,093,719 A | 3/1992 | Prescott | |
| 5,105,269 A | 4/1992 | Nakamura et al. | |
| 5,106,387 A | 4/1992 | Kittrell et al. | |
| 5,109,859 A | 5/1992 | Jenkins | |
| 5,111,804 A | 5/1992 | Funakoshi | |
| 5,113,254 A | 5/1992 | Kanno et al. | |
| 5,121,213 A | 6/1992 | Nishioka | |
| 5,126,639 A | 6/1992 | Srivastava | |
| 5,130,804 A | 7/1992 | Tamura et al. | |
| 5,165,063 A | 11/1992 | Strater et al. | |
| 5,166,656 A | 11/1992 | Badehi et al. | |
| 5,182,672 A | 1/1993 | Mukai et al. | |
| 5,188,093 A | 2/1993 | Lafferty et al. | |
| 5,190,523 A | 3/1993 | Lindmayer | |
| 5,191,203 A | 3/1993 | McKinley | |
| 5,198,894 A | 3/1993 | Hicks | |
| 5,209,219 A | 5/1993 | Hollobaugh | |
| 5,220,198 A | 6/1993 | Tsuji | |
| 5,222,477 A | 6/1993 | Lia | |
| 5,228,430 A | 7/1993 | Sakamoto | |
| 5,258,834 A | 11/1993 | Tsuji et al. | |
| 5,289,434 A | 2/1994 | Berni | |
| 5,290,555 A * | 3/1994 | Guthauser et al. | 424/401 |
| 5,291,010 A | 3/1994 | Tsuji | |
| 5,298,741 A | 3/1994 | Walt et al. | |
| 5,304,173 A | 4/1994 | Kittrell et al. | |
| 5,305,098 A | 4/1994 | Matsunaka et al. | |
| 5,318,024 A | 6/1994 | Kittrell et al. | |
| 5,361,166 A | 11/1994 | Atkinson et al. | |
| 5,365,268 A | 11/1994 | Minami | |
| 5,376,960 A | 12/1994 | Wurster | |
| 5,377,047 A | 12/1994 | Broome et al. | |
| 5,381,784 A | 1/1995 | Adair | |
| 5,396,366 A | 3/1995 | Brown et al. | |
| 5,398,685 A | 3/1995 | Wilk et al. | |
| 5,402,769 A | 4/1995 | Tsuji | |
| 5,408,999 A * | 4/1995 | Singh et al. | 600/342 |
| 5,430,475 A | 7/1995 | Goto et al. | |
| 5,434,615 A | 7/1995 | Matumoto | |
| 5,436,655 A | 7/1995 | Hiyama et al. | |
| 5,438,975 A | 8/1995 | Miyagi et al. | |
| 5,440,669 A | 8/1995 | Rakuljic et al. | |
| 5,450,243 A | 9/1995 | Nishioka | |
| 5,455,455 A | 10/1995 | Badehi | |
| 5,458,612 A | 10/1995 | Chin | |
| 5,459,570 A | 10/1995 | Swanson et al. | |
| 5,469,841 A | 11/1995 | Kobayashi et al. | |
| 5,494,483 A | 2/1996 | Adair | |
| 5,512,940 A | 4/1996 | Takasugi et al. | |
| 5,517,997 A | 5/1996 | Fontenot | |
| 5,531,664 A | 7/1996 | Adachi et al. | |
| 5,547,455 A | 8/1996 | McKenna et al. | |
| 5,547,906 A | 8/1996 | Badehi | |
| 5,594,497 A | 1/1997 | Ahern | |
| 5,603,687 A | 2/1997 | Hori et al. | |
| 5,607,435 A | 3/1997 | Sachdeva et al. | |
| 5,621,574 A | 4/1997 | Foo | |
| 5,630,788 A | 5/1997 | Forkner et al. | |
| 5,647,368 A | 7/1997 | Zeng et al. | |
| 5,662,621 A | 9/1997 | Lafontaine | |
| 5,673,083 A | 9/1997 | Izumi et al. | |
| 5,685,311 A | 11/1997 | Hara | |
| 5,693,043 A * | 12/1997 | Kittrell et al. | 606/15 |
| 5,704,892 A | 1/1998 | Adair | |
| 5,716,323 A | 2/1998 | Lee | |
| 5,716,759 A | 2/1998 | Badehi | |
| 5,722,403 A | 3/1998 | McGee et al. | |
| 5,732,150 A | 3/1998 | Zhou et al. | |
| 5,740,808 A | 4/1998 | Panescu et al. | |
| 5,749,827 A | 5/1998 | Minami | |
| 5,751,340 A | 5/1998 | Strobl et al. | |
| 5,752,518 A | 5/1998 | McGee et al. | |
| 5,769,792 A | 6/1998 | Palcic et al. | |
| 5,772,597 A | 6/1998 | Goldberger et al. | |
| 5,776,049 A | 7/1998 | Takahashi | |
| 5,783,829 A | 7/1998 | Sealock et al. | |
| 5,784,098 A | 7/1998 | Shoji et al. | |
| 5,792,984 A | 8/1998 | Bloom | |
| 5,800,341 A | 9/1998 | McKenna et al. | |
| 5,807,261 A | 9/1998 | Benaron et al. | |
| 5,808,665 A | 9/1998 | Green | |
| 5,818,644 A | 10/1998 | Noda | |
| 5,827,172 A | 10/1998 | Takahashi et al. | |
| 5,827,531 A * | 10/1998 | Morrison et al. | 424/450 |
| 5,840,017 A | 11/1998 | Furusawa et al. | |
| 5,846,185 A | 12/1998 | Carollo et al. | |
| 5,848,969 A | 12/1998 | Panescu et al. | |
| 5,865,729 A | 2/1999 | Meehan et al. | |
| 5,870,229 A | 2/1999 | Tsuchida | |
| 5,873,816 A | 2/1999 | Kagawa et al. | |
| 5,879,285 A | 3/1999 | Ishii | |
| 5,904,651 A | 5/1999 | Swanson et al. | |
| 5,908,445 A | 6/1999 | Whayne et al. | |
| 5,913,817 A | 6/1999 | Lee | |
| 5,916,155 A | 6/1999 | Levinson et al. | |
| 5,929,900 A | 7/1999 | Yamanaka et al. | |
| 5,940,126 A | 8/1999 | Kimura | |
| 5,947,894 A | 9/1999 | Chapman et al. | |

(56) References Cited

U.S. PATENT DOCUMENTS

| | | |
|---|---|---|
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,989,185 A | 11/1999 | Miyazaki |
| 5,998,878 A | 12/1999 | Johnson |
| 5,999,327 A | 12/1999 | Nagaoka |
| 6,008,123 A | 12/1999 | Kook et al. |
| 6,014,919 A | 1/2000 | Jacobsen et al. |
| 6,022,758 A | 2/2000 | Badehi |
| 6,040,235 A | 3/2000 | Badehi |
| 6,059,760 A | 5/2000 | Sandmore et al. |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Tearney et al. |
| 6,139,489 A | 10/2000 | Wampler et al. |
| 6,139,819 A * | 10/2000 | Unger et al. ............. 424/9.52 |
| 6,142,930 A | 11/2000 | Ito et al. |
| 6,161,035 A | 12/2000 | Furusawa |
| 6,184,923 B1 | 2/2001 | Miyazaki |
| 6,193,908 B1 * | 2/2001 | Hampden-Smith et al. ............. 252/301.4 R |
| 6,211,955 B1 | 4/2001 | Basiji et al. |
| 6,224,969 B1 * | 5/2001 | Steenbergen et al. ...... 428/313.3 |
| 6,261,226 B1 | 7/2001 | McKenna et al. |
| 6,262,855 B1 | 7/2001 | Greisz |
| 6,271,206 B1 * | 8/2001 | Pillai et al. ............. 514/44 R |
| 6,280,960 B1 * | 8/2001 | Carr ............................. 435/7.2 |
| 6,288,172 B1 | 9/2001 | Goetz et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsue |
| 6,361,491 B1 | 3/2002 | Hasegawa et al. |
| 6,366,726 B1 | 4/2002 | Wach et al. |
| 6,375,635 B1 | 4/2002 | Moutafis et al. |
| 6,384,397 B1 | 5/2002 | Takiar et al. |
| 6,384,884 B1 | 5/2002 | Nakamura et al. |
| 6,396,116 B1 | 5/2002 | Kelly et al. |
| 6,407,768 B1 | 6/2002 | Ishikawa |
| 6,445,939 B1 | 9/2002 | Swanson et al. |
| 6,456,423 B1 | 9/2002 | Nayfeh et al. |
| 6,471,636 B1 | 10/2002 | Sano et al. |
| 6,485,413 B1 | 11/2002 | Boppart et al. |
| 6,522,913 B2 | 2/2003 | Swanson et al. |
| 6,525,866 B1 * | 2/2003 | Lin et al. ............. 359/296 |
| 6,533,722 B2 | 3/2003 | Nakashima |
| 6,537,205 B1 * | 3/2003 | Smith ............................. 600/104 |
| 6,551,302 B1 * | 4/2003 | Rosinko et al. ............. 604/505 |
| 6,552,796 B2 | 4/2003 | Magnin et al. |
| 6,561,972 B2 | 5/2003 | Ooshima et al. |
| 6,570,659 B2 | 5/2003 | Schmitt |
| 6,573,950 B1 | 6/2003 | Hairata et al. |
| 6,585,717 B1 | 7/2003 | Wittenberger et al. |
| 6,595,913 B2 | 7/2003 | Takahashi |
| 6,618,614 B1 | 9/2003 | Chance et al. |
| 6,622,367 B1 | 9/2003 | Tu et al. |
| 6,643,071 B2 | 11/2003 | Schnitzer |
| 6,658,279 B2 | 12/2003 | Swanson et al. |
| 6,659,941 B2 | 12/2003 | Weber et al. |
| 6,695,787 B2 | 2/2004 | Hogendijk et al. |
| 6,710,919 B1 * | 3/2004 | Clausen ............................. 359/453 |
| 6,719,686 B2 | 4/2004 | Coakley et al. |
| 6,727,313 B2 | 4/2004 | Zhou et al. |
| 6,756,437 B1 * | 6/2004 | Xue et al. ............. 524/401 |
| 6,761,684 B1 | 7/2004 | Speier |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 * | 5/2005 | Intintoli et al. ............. 606/2 |
| 6,894,729 B2 | 5/2005 | Hirata et al. |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 | 9/2005 | Yamaguchi et al. |
| 6,944,204 B2 | 9/2005 | Zhou et al. |
| 6,953,432 B2 | 10/2005 | Schiefer |
| 6,956,624 B2 | 10/2005 | Hirata et al. |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 | 7/2006 | Hirata et al. |
| 7,091,500 B2 | 8/2006 | Schnitzer |
| 7,098,871 B1 | 8/2006 | Tegreene et al. |
| 7,102,817 B1 | 9/2006 | Wu |
| 7,108,657 B2 | 9/2006 | Irion et al. |
| 7,153,299 B1 | 12/2006 | Tu et al. |
| 7,165,552 B2 | 1/2007 | Deem et al. |
| 7,166,537 B2 | 1/2007 | Jacobsen et al. |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,247,847 B2 | 7/2007 | Webb et al. |
| 7,304,310 B1 | 12/2007 | Shortt et al. |
| 7,393,321 B2 | 7/2008 | Doguchi et al. |
| 7,420,675 B2 | 9/2008 | Giakos |
| 7,511,891 B2 | 3/2009 | Messerschmidt |
| 7,554,597 B2 | 6/2009 | Scherling |
| 7,591,780 B2 | 9/2009 | Jacobsen |
| 7,629,659 B2 | 12/2009 | Jacobsen |
| 7,787,939 B2 | 8/2010 | Jacobsen et al. |
| 7,823,215 B2 | 10/2010 | Giakos |
| 7,835,074 B2 | 11/2010 | Jacobsen et al. |
| 7,842,046 B1 | 11/2010 | Nakao |
| 7,901,870 B1 | 3/2011 | Wach |
| 2001/0007051 A1 | 7/2001 | Nakashima |
| 2001/0007511 A1 | 7/2001 | Minami et al. |
| 2001/0012053 A1 * | 8/2001 | Nakamura ............. 348/45 |
| 2001/0024848 A1 | 9/2001 | Nakamura |
| 2001/0049509 A1 | 12/2001 | Sekine et al. |
| 2002/0007110 A1 | 1/2002 | Irion |
| 2002/0034537 A1 * | 3/2002 | Schulze et al. ............. 424/450 |
| 2002/0039594 A1 * | 4/2002 | Unger ............. 424/426 |
| 2002/0080248 A1 | 6/2002 | Adair et al. |
| 2002/0109774 A1 | 8/2002 | Meron et al. |
| 2002/0111534 A1 | 8/2002 | Suzuki et al. |
| 2002/0166946 A1 | 11/2002 | Iizuka et al. |
| 2002/0168776 A1 * | 11/2002 | Cizdziel et al. ............. 436/95 |
| 2002/0188204 A1 | 12/2002 | McNamara |
| 2002/0193660 A1 | 12/2002 | Weber |
| 2003/0071342 A1 | 4/2003 | Honda et al. |
| 2003/0092995 A1 | 5/2003 | Thompson |
| 2003/0114732 A1 * | 6/2003 | Webler et al. ............. 600/121 |
| 2003/0197812 A1 | 10/2003 | Hirata et al. |
| 2003/0199761 A1 | 10/2003 | Yock |
| 2003/0202127 A1 | 10/2003 | Hirata et al. |
| 2003/0208211 A1 | 11/2003 | Kortenbach |
| 2003/0220574 A1 | 11/2003 | Markus |
| 2003/0222325 A1 | 12/2003 | Jacobsen |
| 2004/0006274 A1 * | 1/2004 | Giller et al. ............. 600/473 |
| 2004/0015049 A1 | 1/2004 | Zaar |
| 2004/0017961 A1 | 1/2004 | Petersen et al. |
| 2004/0059204 A1 | 3/2004 | Marshall |
| 2004/0097804 A1 | 5/2004 | Sobe |
| 2004/0111031 A1 | 6/2004 | Alfano et al. |
| 2004/0115955 A1 * | 6/2004 | Motoyama et al. ............. 438/781 |

(56) References Cited

U.S. PATENT DOCUMENTS

| | | |
|---|---|---|
| 2004/0165858 A1 | 8/2004 | Curatolo |
| 2004/0181148 A1 | 9/2004 | Uchiyama et al. |
| 2004/0222031 A1 | 11/2004 | Szalony et al. |
| 2004/0225222 A1 | 11/2004 | Zeng et al. |
| 2004/0257566 A1* | 12/2004 | Chism, II ............ 356/369 |
| 2004/0260148 A1 | 12/2004 | Schnitzer |
| 2005/0054902 A1 | 3/2005 | Konno |
| 2005/0065504 A1 | 3/2005 | Melsky et al. |
| 2005/0084229 A1* | 4/2005 | Babbitt et al. ............ 385/146 |
| 2005/0088576 A1 | 4/2005 | Hirata et al. |
| 2005/0099824 A1* | 5/2005 | Dowling et al. ............ 362/572 |
| 2005/0124875 A1 | 6/2005 | Kawano et al. |
| 2005/0152421 A1 | 7/2005 | Fujitani |
| 2005/0154277 A1 | 7/2005 | Tang et al. |
| 2005/0158899 A1 | 7/2005 | Jacobsen et al. |
| 2005/0171521 A1* | 8/2005 | Brucker et al. ............ 606/15 |
| 2005/0174649 A1 | 8/2005 | Okada et al. |
| 2005/0187568 A1 | 8/2005 | Klenk et al. |
| 2005/0197534 A1 | 9/2005 | Barbato et al. |
| 2005/0226636 A1* | 10/2005 | Hiramatsu et al. ............ 398/182 |
| 2005/0231718 A1 | 10/2005 | Goodall et al. |
| 2005/0234345 A1 | 10/2005 | Yang |
| 2005/0264813 A1 | 12/2005 | Giakos |
| 2005/0267340 A1 | 12/2005 | Ishihara et al. |
| 2005/0288555 A1 | 12/2005 | Binmoeller |
| 2006/0009682 A1 | 1/2006 | Nagasawa et al. |
| 2006/0013593 A1 | 1/2006 | Yokoo et al. |
| 2006/0017928 A1 | 1/2006 | Crowther |
| 2006/0051036 A1 | 3/2006 | Treado |
| 2006/0069312 A1 | 3/2006 | O'Connor |
| 2006/0079835 A1 | 4/2006 | Frassica |
| 2006/0135921 A1* | 6/2006 | Wiercinski et al. ............ 604/368 |
| 2006/0142700 A1 | 6/2006 | Sobelman et al. |
| 2006/0146172 A1 | 7/2006 | Jacobsen et al. |
| 2006/0181774 A1* | 8/2006 | Ojima et al. ............ 359/586 |
| 2006/0252994 A1 | 11/2006 | Ratnakar |
| 2006/0253088 A1 | 11/2006 | Chow et al. |
| 2007/0010709 A1 | 1/2007 | Reinschke |
| 2007/0032796 A1 | 2/2007 | Chin-Chen et al. |
| 2007/0073321 A1 | 3/2007 | Mikkaichi et al. |
| 2007/0083232 A1 | 4/2007 | Lee |
| 2007/0135803 A1 | 6/2007 | Belson |
| 2007/0146887 A1* | 6/2007 | Ikeda et al. ............ 359/586 |
| 2007/0208252 A1 | 9/2007 | Makower |
| 2007/0228300 A1 | 10/2007 | Smith |
| 2007/0233187 A1 | 10/2007 | Lobello |
| 2007/0239066 A1 | 10/2007 | Laham et al. |
| 2007/0255392 A1 | 11/2007 | Johnson |
| 2007/0293727 A1 | 12/2007 | Goldfarb et al. |
| 2008/0045794 A1 | 2/2008 | Belson |
| 2008/0058601 A1 | 3/2008 | Fujimori |
| 2008/0071141 A1 | 3/2008 | Gattani et al. |
| 2008/0094326 A1* | 4/2008 | Yamaki et al. ............ 345/87 |
| 2008/0114309 A1 | 5/2008 | Zuckerman |
| 2008/0160257 A1* | 7/2008 | Takada et al. ............ 428/145 |
| 2008/0177141 A1 | 7/2008 | Wu et al. |
| 2008/0183080 A1 | 7/2008 | Abraham |
| 2008/0188767 A1 | 8/2008 | Oaki et al. |
| 2008/0227893 A1* | 9/2008 | Tamori et al. ............ 524/66 |
| 2008/0267562 A1* | 10/2008 | Wang et al. ............ 385/31 |
| 2009/0027765 A1 | 1/2009 | Kamijima |
| 2009/0036764 A1 | 2/2009 | Rivas et al. |
| 2009/0054791 A1 | 2/2009 | Flusberg |
| 2009/0082626 A1 | 3/2009 | Ichimura et al. |
| 2009/0119808 A1 | 5/2009 | Giakos |
| 2009/0137928 A1 | 5/2009 | Quick et al. |
| 2009/0143645 A1 | 6/2009 | Matthes |
| 2009/0155371 A1* | 6/2009 | Sojka et al. ............ 424/497 |
| 2009/0156899 A1 | 6/2009 | Konishi |
| 2009/0180197 A1 | 7/2009 | Jacobsen et al. |
| 2009/0213894 A1 | 8/2009 | Grapov et al. |
| 2009/0234325 A1 | 9/2009 | Rozenberg et al. |
| 2009/0267270 A1* | 10/2009 | Murakami et al. ............ 264/447 |
| 2009/0287048 A1 | 11/2009 | Jacobson et al. |
| 2010/0085567 A1 | 4/2010 | Dottery et al. |
| 2010/0106134 A1 | 4/2010 | Jolly et al. |
| 2010/0134872 A1* | 6/2010 | Johnson et al. ............ 359/296 |
| 2010/0171821 A1 | 7/2010 | Jacobsen et al. |
| 2010/0248178 A1 | 9/2010 | Nahlieli |
| 2011/0204265 A1 | 8/2011 | Smith et al. |

FOREIGN PATENT DOCUMENTS

| | | |
|---|---|---|
| DE | 19859434 | 7/2000 |
| EP | 0482997 | 4/1992 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1488737 | 12/2004 |
| EP | 1626436 | 2/2006 |
| EP | 1647569 A1 * | 4/2006 |
| EP | 1880656 | 1/2008 |
| JP | 58-046924 | 3/1983 |
| JP | 63-155115 | 6/1988 |
| JP | H05-039501 | 2/1993 |
| JP | 5-049602 | 3/1993 |
| JP | H07-148105 | 6/1995 |
| JP | H07-222712 | 8/1995 |
| JP | 08-076028 | 3/1996 |
| JP | 08084700 | 4/1996 |
| JP | H09-021963 | 1/1997 |
| JP | 11 137512 | 5/1999 |
| JP | 2001/314365 | 11/2001 |
| JP | 2004-086553 | 3/2004 |
| JP | 2004/329700 | 11/2004 |
| JP | 2005334462 | 8/2005 |
| JP | 2006/162418 | 6/2006 |
| JP | 2006/320369 | 11/2006 |
| JP | 2007-167387 | 7/2007 |
| JP | 2007/312290 | 11/2007 |
| JP | 2009/067946 | 4/2009 |
| KR | 10-20080027935 | 3/2008 |
| WO | WO98/38907 | 9/1998 |
| WO | WO99/40624 | 8/1999 |
| WO | WO00/54033 | 9/2000 |
| WO | WO 03/081831 | 10/2003 |
| WO | WO2006/060777 | 6/2006 |
| WO | WO2007008876 | 1/2007 |
| WO | WO 2007/138889 | 12/2007 |

OTHER PUBLICATIONS

PCT Application PCT/US2010/051200; filed Oct. 1, 2010; Stephen C. Jacobsen; ISR mailed Jun. 3, 2011.

PCT Application PCT/US2010/051198; filed Oct. 1, 2010; Stephen C. Jacobsen; ISR mailed Jun. 3, 2011.

PCT Application PCT/US2010/051192; filed Oct. 1, 2010; Stephen C. Jacobsen; ISR mailed May 30, 2011.

Boppart, S.A. et al., "Forward-imaging instruments for optical coherence tomography." Optics Letters, Nov. 1, 1997, vol. 22, No. 21, pp. 1618-1620.

Boppart, S.A. et al., "Optical imaging technology in minimally invasive surgery," Surg. Endosc., 1999, vol. 13, pp. 718-722.

Fujimoto, JG et al., "High resolution in vivo intra-arterial imaging with optical coherence tomography," Heart, 1999, vol. 82, pp. 128-133.

Hirofumi Tsuchida et al., "Design of imaging lens systems that use low dispersive radial gradient-index rod," Jpn, J. Appl. Phys. vol. 37 No. 6B, Jun. 30, 1998, pp. 3633-3637.

http://news.thomasnet.com/fullstory/23462, "Near-IR_Camera_Utilizes_CCD_Array_with_Phosphor_Coating"; Jun. 11, 2003; 5 pages.

J. Knittel et al., "Endoscope-compatible confocal microscope using a gradient index-lens system" Optics Communications, vol. 188, Issue 5-6, Feb. 2001, pp. 267-273.

Jacobsen, Stephen C., U.S. Appl. No. 10/391,489, filed Mar. 17, 2003.

Jacobsen, Stephen C., U.S. Appl. No. 10/391,490, filed Mar. 17, 2003.

(56) References Cited

OTHER PUBLICATIONS

Jacobsen, Stephen C., U.S. Appl. No. 10/391,513, filed Mar. 17, 2003.
Jacobsen, Stephen C., U.S. Appl. No. 11/292,902, filed Dec. 1, 2005.
Jacobsen, Stephen C., U.S. Appl. No. 11/810,702, filed Jun. 5, 2007.
Jacobsen, Stephen C., U.S. Appl. No. 12/008,486, filed Jan. 11, 2008.
Jacobsen, Stephen C., U.S. Appl. No. 12/079,741, filed Mar. 27, 2008.
Jacobsen, Stephen C., U.S. Appl. No. 12/152,730, filed May 16, 2008.
Jacobsen, Stephen C., U.S. Appl. No. 12/487,481, filed Jun. 18, 2009.
Jacobsen, Stephen C., U.S. Appl. No. 12/487,495, filed Jun. 18, 2009.
Jacobsen, Stephen C., U.S. Appl. No. 12/512,188, filed Jul. 30, 2009.
Jacobsen, Stephen C.; U.S. Appl. No. 12/611,776, filed Nov. 3, 2009.
Jacobsen, Stephen C.; U.S. Appl. No. 12/792,562, filed Jun. 2, 2010.
Jacobsen, Stephen C.; U.S. Appl. No. 12/896,731, filed Oct. 1, 2010.
Jacobsen, Stephen C.; U.S. Appl. No. 12/896,732, filed Oct. 1, 2010.
Jacobsen, Stephen C.; U.S. Appl. No. 12/896,737, filed Oct. 1, 2010.
Jacobsen, Stephen C.; U.S. Appl. No. 12/938,672, filed Nov. 3, 2010.
Jacobsen, Stephen C.; U.S. Appl. No. 12/946,442, filed Nov. 15, 2010.
Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.
Literature from Grin Tech, "In vivo medical confocal imaging and optical coherence tomography," www.grintech.de, Revision Jun. 2001, pp. 1-3.
Microcam, Minast Project 5.04, Nov. 11, 1999, http://www.imt.unine.ch/ESPLAB/www/projects/Microcam/, pp. 1-16.
Nguyen, Clark, "Communications Applications of Microelectromechanical Systems," Proceedings, Sensors Expo, May 19-21, 1998, San Jose, CA. pp. 447-455.
Tearney, G.J. et al., "Scanning single-mode fiber optic catheter-endoscope for optical coherence tomography," Optics Letters, Apr. 1, 1996, vol. 21, No. 7, pp. 543-545.
Zeis, Michael et al., "Color Business Report," ISSN 1055-3339. Jul. 2002, p. 5.
U.S. Appl. No. 12/487,481, filed Jun. 18, 2009; Stephen C. Jacobsen; office action dated Oct. 12, 2012.
U.S. Appl. No. 12/512,188, filed Jul. 30, 2009; Stephen C. Jacobsen; office action dated Nov. 19, 2012.
PCT Application PCT/US2010/051188; filed Oct. 1, 2010; Stephen C. Jacobsen; International Search Report mailed Jul. 13, 2011.
Xie et al; GRIN Lens Rod Based Probe for Endoscopic Spectral Domain Optical Coherence Tomography with Fast Dynamic Focus Tracking; Optics Express; Apr. 17, 2006; 9 pages; vol. 14, No. 8.
Xuting Technologies Co., Ltd.; http://www.xutingby.com/en/products/glinfo:htm; as accessed May 1, 2008; 5 pages.
Frequency; Wikipedia, The Free Encyclopedia; http://en.wikipedia.org/wiki/Frequency; as accessed May 9, 2008; 4 pages.
Introduction to Gradient Index Optics; http://grintech.de/e_main_grin.htm; as accessed May 1, 2008; 7 pages.
Gradient Index (GRIN) Lenses; Grin Tech; 2 pages; The Applicant believes the year of publication of this article is prior to the effective US filing date of this patent application.
Shape Memory Polymers—Biodegradable Sutures; http://www.azom.com/details.asp?ArticleID=1542; as accessed Nov. 6, 2007; 4 pages.
Surgical Needles for Use With Sutures; Wikipedia, The Free Encyclopedia; as accessed Nov. 6, 2007; 6 pages.
Harder et al; Against the Migraine; Science News Online; http://www.sciencenews.org/articles/20050219/bob8.asp; Feb. 19, 2005; 11 pages.
U.S. Appl. No. 12/152,730, filing date May 16, 2008; Stephen C. Jacobson; office action issued Sep. 16, 2011.
Gaoping et al.; Research on the Measurement of Grin Lens Focused Spot Diameter and Resolution; Applied Optics; 1995; vol. 16, No. 6.

\* cited by examiner

LIGHT DIFFUSION APPARATUS

CLAIM OF PRIORITY

This application claims priority to U.S. Provisional Application No. 61/247,892 filed on Oct. 1, 2009 which is incorporated herein by reference in its entirety.

BACKGROUND

Minimally invasive diagnostic medical procedures are used to assess the interior surfaces of an organ by inserting a tube into the body. The instruments utilized may have a rigid or flexible tube and provide an image for visual inspection and photography, but also enable taking biopsies and retrieval of foreign objects. Analysis of image data collected during the inspection and photography of the interior of the body cavity is a critical component of proper diagnosis of disease and other related conditions.

Percutaneous catheterization is a type of medical treatment that is generally less-invasive than directly accessing an internal body site for treatment, such as when using general surgery methods. In catheterization techniques, a long tubular catheter is introduced into the body through a puncture site. It is then passed to an internal body site, usually through passageways such as the vascular tree. Treatment or diagnostic procedures may then be accomplished using the catheter by manipulation of the portion of the catheter remaining outside the body.

Some medical imaging devices utilize laser sources coupled to a fiber optic light guide to illuminate a target to be imaged. The nature of the light emitted from the fiber can result in hot spots in the center of the image, image speckle, and lack of illumination on the periphery of the target.

SUMMARY OF THE INVENTION

It has been recognized that it would be advantageous to develop a light diffusing composition that provides an even illumination to optimize image clarity from a SSID. In one embodiment of the present invention, a light diffusing composition comprises a translucent matrix comprising a plurality of hollow micro particles. The plurality of hollow micro particles are dispersed throughout the translucent matrix and a fluid is disposed within the hollow micro particle. The refractive index of the fluid within the hollow micro particle is different than a refractive index of the translucent matrix.

In one aspect of the present invention, the refractive index of the fluid is less than the refractive index of the translucent matrix. In yet another aspect, the absolute value of the difference between the refractive index of the fluid and the refractive index of the translucent matrix is greater than approximately 0.4. In an additional embodiment, the refractive index of the fluid is greater than 1.0. In yet another embodiment, the refractive index of the fluid is less than the refractive index of the shell of the micro particle. In still another embodiment, the refractive index of the fluid is greater than the refractive index of the translucent matrix.

In one embodiment of the present invention, a light diffusing composition is disclosed comprising an opaque matrix comprising a plurality of hollow micro particles, the plurality of hollow micro particles being dispersed throughout the opaque matrix. A fluid is disposed within the hollow micro particle, wherein, a refractive index of the fluid within the hollow micro particle is different than a refractive index of the opaque matrix.

According to one embodiment of the present invention, a medical imaging device is disclosed comprising a SSID operatively coupled to a lens system. The medical imaging device further comprises a light source configured to propagate light near the lens system and a matrix disposed on a distal end of the light source. The matrix comprises a plurality of fluid-filled compartments, wherein a refractive index of the fluid is different than a refractive index of the matrix.

In one aspect, the light source of the medical imaging device is oriented in a direction substantially parallel to an image plane of the SSID. In an additional aspect, the matrix is a translucent matrix. In yet another aspect, the matrix is an opaque matrix. In yet another aspect, the absolute value of the difference between the refractive index of the fluid and the refractive index of the matrix is greater than approximately 0.4. In still another aspect, the matrix occludes the distal end of the elongated hollow member.

According to an additional embodiment of the present invention, a medical imaging device is disclosed comprising a SSID operatively coupled to a lens system and a light source configured to propagate light near the lens system. A translucent matrix is disposed on a distal end of the light source. The translucent matrix comprises a plurality of micro spheres dispersed throughout the translucent matrix, the micro spheres having a reflective outer surface.

In one embodiment of the present invention, a method of improving the image clarity of a miniature imaging device is disclosed. The method comprises providing a SSID operatively coupled to a lens system and a light source configured to propagate light near the lens system. The method further comprises propagating light through a translucent matrix and onto a target surface. The translucent matrix comprises a plurality of fluid-filled compartments, wherein a refractive index of the fluid is different than a refractive index of the translucent matrix. The method further comprises receiving light reflected from the target surface through the lens system and onto the SSID.

In one aspect of the present invention, the refractive index of the fluid is less than the refractive index of the translucent matrix. In another aspect, the absolute value of the difference between the refractive index of the fluid and the refractive index of the translucent matrix is greater than approximately 0.4. In still another aspect, the refractive index of the fluid is greater than the refractive index of the translucent matrix. In one embodiment of the present invention, the fluid is air. In still another embodiment, the translucent matrix consists of a pressure sensitive adhesive or structural adhesive.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 8 a-c are side views of a light fiber and diffuser showing the diffusive affects of one embodiment of the present invention;

DETAILED DESCRIPTION OF EXAMPLE EMBODIMENT(S)

Reference will now be made to, among other things, the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," "SSID chip," or "solid state imaging chip" in the exemplary embodiments generally comprises an imaging array or pixel array for gathering image data. In one embodiment, the SSID can comprise a silicon or silicon-like substrate or amorphous silicon thin film transistors (TFT) having features typically manufactured therein. Features can include the imaging array, conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. Typically, an umbilical includes a conductive line, such as electrical wire(s) or other conductors, for providing power, ground, clock signal, and output signal with respect to the SSID, though not all of these are strictly required. For example, ground can be provided by another means than through an electrical wire, e.g., to a camera housing such as micromachined tubing, etc. The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "GRadient refractive INdex lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the effects of a more traditionally shaped lens.

"Matrix" refers to a surrounding substance within which something else is contained. In one embodiment, such a matrix comprises an opaque adhesive. In yet another embodiment, the matrix comprises a translucent adhesive or an opaque adhesive. It is understood that the matrix may comprise any material suitable for housing diffusive elements described further herein to create the desired diffusive effect.

With these definitions in mind, reference will now be made to, among other things, the accompanying drawings, which illustrate, by way of example, embodiments of the invention.

Figure 1:
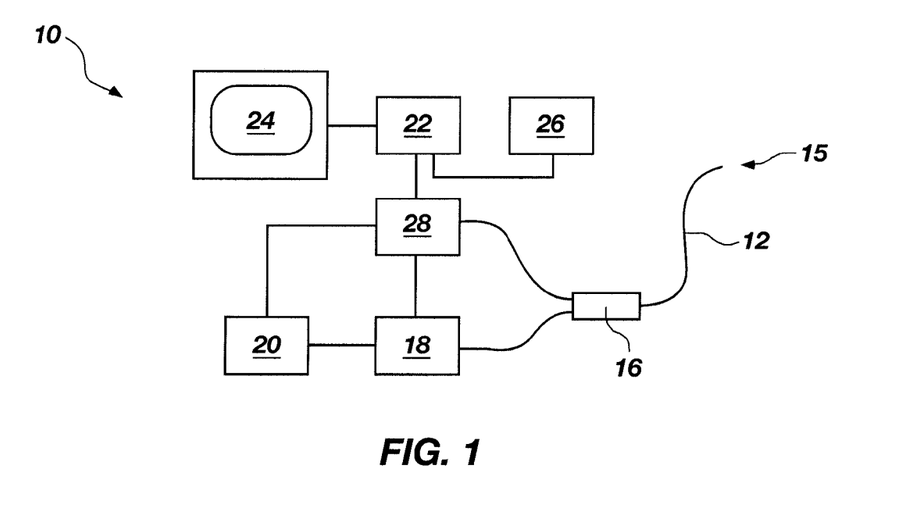
FIG. 1 is an exemplary view of a medical imaging system in accordance with an embodiment of the present invention.

Referring now to FIG. 1, in one embodiment of the present invention, a medical imaging system 10 is disclosed comprising a micro-catheter 12 having an imaging device disposed at a distal tip 15 of the micro-catheter 12. A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device 14 and feeds a digital image signal to the processor based on a signal received from the imaging device via an electrical umbilical, including conductive wires through the micro-catheter 12. A light source may also be provided at the distal end of the micro-catheter 12. In one aspect, the system further includes a fitting 16 enabling an imaging fluid, such as a clear saline solution, to be dispensed to the distal tip portion of the micro-catheter 12 from a reservoir 18 through an elongated tubular member removably attached to the micro-catheter 12 or through a lumen of the micro-catheter 12 to displace body fluids as needed to provide a clearer image. Fluids may be pumped to the distal end of the micro-catheter for other reasons described herein. A pump 20 is provided, and is manually actuated by a medical practitioner performing a medical imaging procedure, or can be automated and electronically controlled so as to dispense fluid on demand according to control signals from the practitioner, sensors, or according to software commands.

Figure 2:
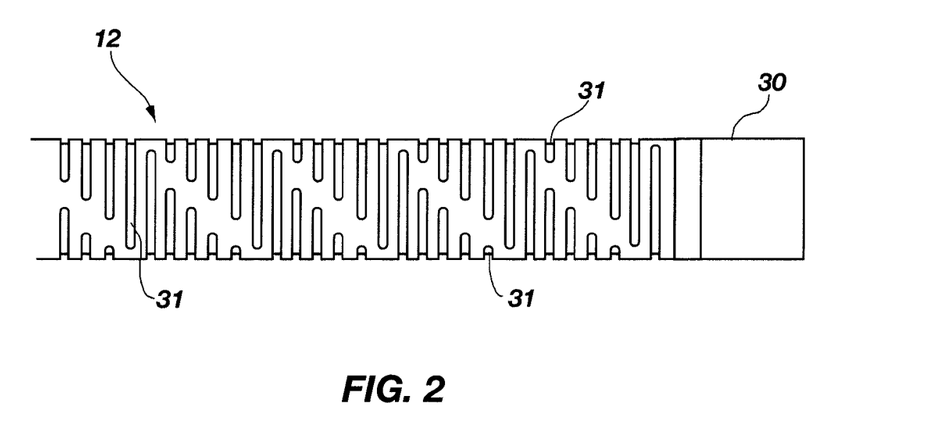
FIG. 2 is a side view of a micro-catheter in accordance with one embodiment of the present invention.
Figure 3:
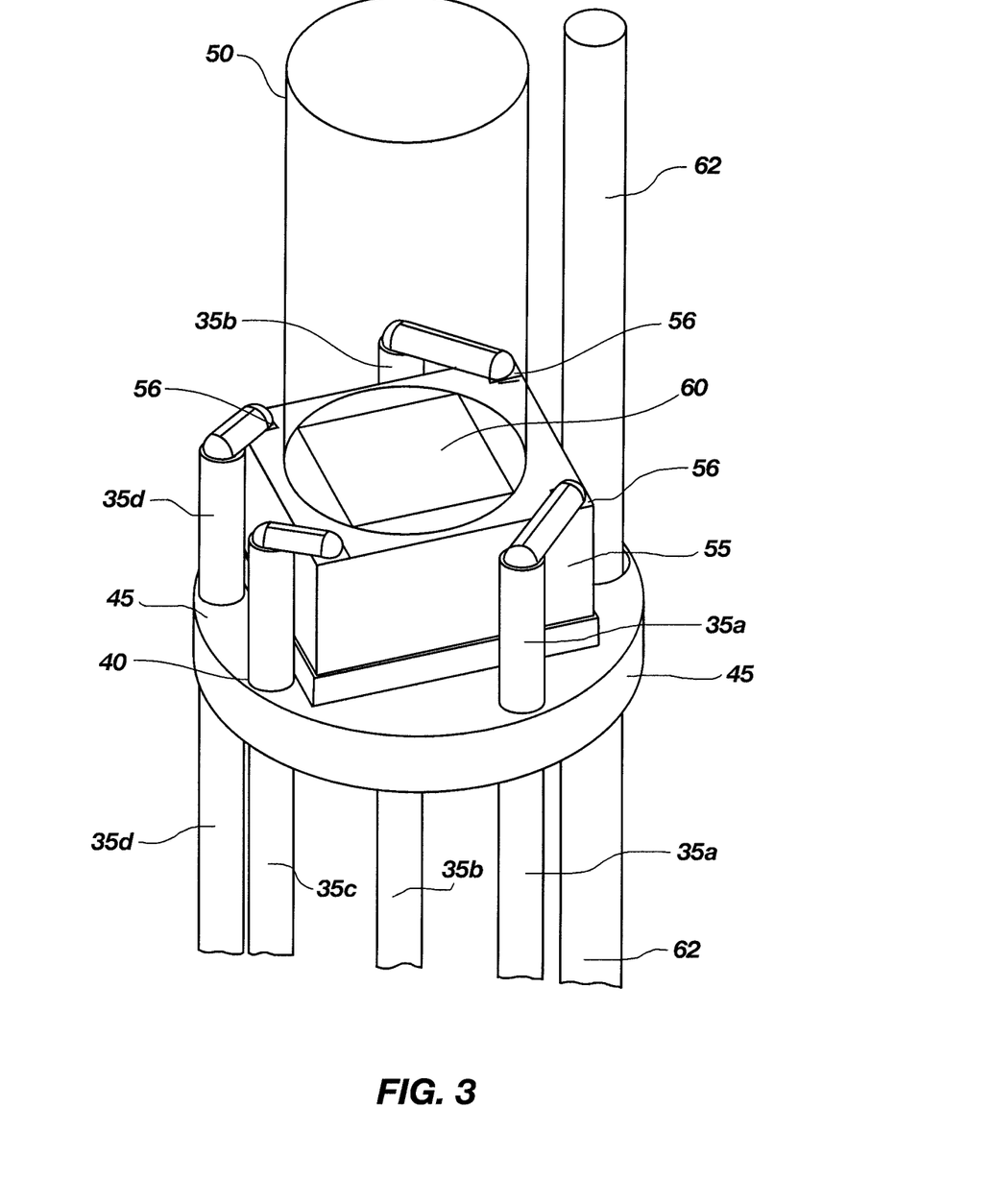
FIG. 3 is a perspective view of an imaging structure according to one embodiment of the present invention.

With reference now to FIGS. 2 and 3, according to one embodiment of the present invention, an imaging device 30 is disposed on a distal end of a micro-catheter 12. Micro-machined cuts 13 are disposed non parallel to a longitudinal direction of the micro-catheter 12 to enable a user, such as a medical practitioner, to guide and steer the distal end of the micro-catheter 12 within a cavity of a patient. In yet another aspect of the present invention, the micro-catheter 12 may incorporate structure and principles of operation from a micro-catheter disclosed in U.S. Pat. No. 6,014,919 to Jacobsen et al., which is incorporated herein by reference in its entirety.

In one aspect of the invention, imaging device 30 comprises at least two conductive wires 35a, 35b for conducting electronic image data to the data processor 22 and for securing an imaging structure 36 between the at least two conductive wires 35a, 35b. As illustrated in FIG. 3 however, a plurality of conductive wires 35a, 35b, 35c, 35d may be utilized. The at least two conductive wires 35a, 35b are oriented along a longitudinal axis of the imaging structure 36 and are disposed within alignment apertures 40 of a planar support member 45. The planar support member 45 comprises at least two alignment apertures 40 disposed on opposing sides of the planar support member 45. The alignment apertures 40 are configured to receive and align the at least two conductive wires 35a, 35b along the longitudinal axis of the imaging structure 36. The imaging structure 36 is at least partially secured between the at least two conductive wires 35a, 35b and is disposed adjacent a top surface of the planar support member 45. In one aspect of the invention, the imaging structure 36 comprises a GRIN lens 50 optically coupled to a SSID 55 and disposed adjacent the SSID 55. The imaging structure further comprises an imaging array 60 disposed on a top surface of the SSID 55. In one embodiment, the GRIN lens 50 is positioned directly on top of the imaging array 60 of the SSID 55.

The at least two conductive wires 35a, 35b are operatively coupled to the imaging structure 36 and are configured to align the imaging structure 36 there between. In one aspect, the conductive wires 35a, 35b are bonded to the imaging structure 36 at contact points 56 disposed on the periphery of a top surface of the SSID 55. In yet another embodiment, the conductive wires, 35a, 35b are bonded to a side surface of the SSID 55.

In one embodiment, the alignment apertures 40 are oriented perpendicular to the top surface of the planar support member 45. However, the alignment apertures may also be disposed in any orientation which is not non-parallel to the planar support member 45 as required to optimally align the imaging structure 36 as desired. In one embodiment, the imaging structure is mounted and aligned such that the image plane of the imaging structure 36 is non parallel to a longitudinal axis of the micro-catheter 12. In one aspect of the invention, a light source (e.g., a fiber optic member, LED, etc.) 62 is disposed within an aperture of the planar support member 40 to provide light for imaging. In yet another aspect of the present invention, the imaging structure 30 may incorporate structure and principles of operation from an imaging device disclosed in U.S. Pat. No. 7,166,537 to Jacobsen et al., which is incorporated herein by reference in its entirety.

Figure 4:
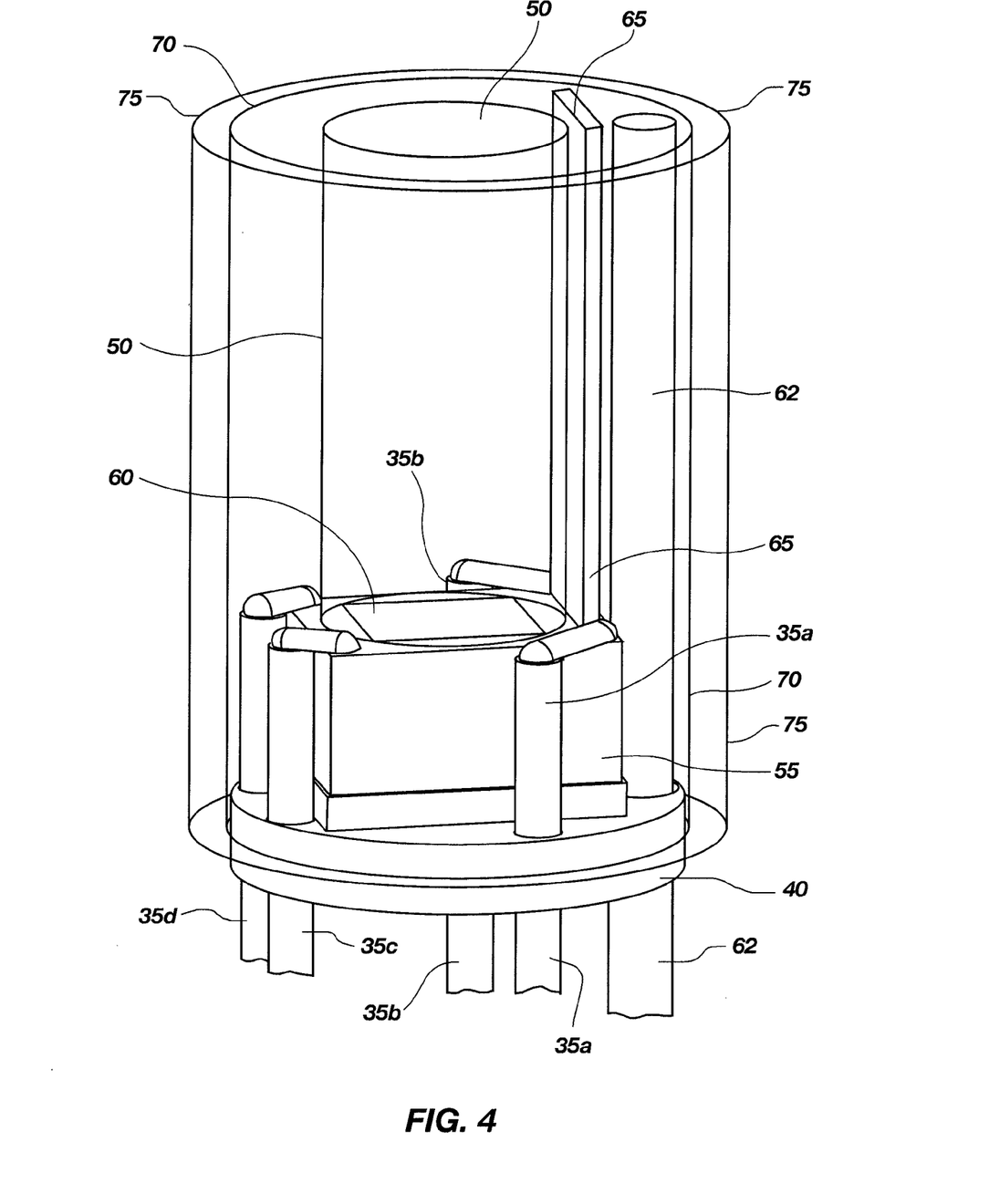
FIG. 4 is a perspective view of an imaging structure according to one embodiment of the present invention.

Referring now to FIGS. 3 and 4, in yet another embodiment of the present invention, the imaging device 30 further comprises a light shield 65. In one aspect, the light shield 65 is bonded to a top surface of the SSID 55. In another aspect, the light shield 65 is bonded to a side surface of the SSID 55. In yet another aspect, the light shield 65 is bonded to a top surface of the planar support member 40. In any event, the light shield 65 is oriented adjacent a side surface of the GRIN lens 50 to minimize stray light from entering the GRIN lens 50 during operation and to ensure proper alignment of the GRIN lens 50 on the imaging array 60 during operation and/or construction of the device. In one aspect of the invention, a first sleeve member 70 is disposed about the imaging structure 36. An adhesive is disposed within the first sleeve member 70 securing the components of the imaging structure 36 in place as well as securing the first sleeve member 70 to the imaging structure 36. In an additional embodiment, a second sleeve member 75 is disposed about the first sleeve member 70 and secured with an adhesive. In one aspect of the invention, the second sleeve member 75 comprises an opaque material to eliminate secondary light from impacting image quality.

In one aspect of the invention, the angle enclosing a cone of light emitted from the light source 62 is determined by the numerical aperture of the light source 62. In one embodiment, the numerical aperture of the light source 62 is approximately 0.22 resulting in an angle of approximately twenty-five degrees. In one aspect of the invention, lens systems used herein have an image capture angle of approximately sixty degrees. Thus, light from an undiffused light source results in hot spots, image speckle, and/or inadequate illumination on the periphery of the image capture area.

Referring now specifically to FIGS. 3 through 6, a light diffusing composition 80 to optimize image clarity is disposed within a distal end of the light source 62. In one embodiment of the present invention, the light diffusing composition 80 comprises a matrix 85 comprising a plurality of hollow micro-particles 90. The matrix 85 may comprise either a translucent or opaque material as desired for a particular application. The plurality of hollow micro particles 90 are dispersed throughout the matrix 85 and a fluid is disposed within the hollow micro-particles 90. A refractive index of the fluid within the hollow micro-particle 90 is different than a refractive index of the matrix 85.

Advantageously, the hollow micro particles 90 allow for predictable and controllable distribution of refractive indices within the matrix thereby optimizing light diffusion. In this manner an increase in illumination uniformity can be achieved, especially when viewing objects at close distances. In one aspect, the refractive index of fluid within micro particles 90 varies from particle to particle or is substantially equivalent throughout all of the micro-particles 90 as is desired for a particular application. Additionally, the density of the micro-particles 90 within the matrix 85 depends on a particular application. For example, in one embodiment, the volumetric density of micro-particles 90 within the matrix 85 ranges from 0.5 to 1.5 with a nominal value of 1. In one aspect of the invention, the amount of resulting diffusion scales with the volumetric density of the micro-particles within the matrix. Thus the amount of diffusion can be optimized by varying the density of the micro-particles. Variations in the path length and angular distribution of the light rays emitted from the distal end of a light source 62 (due to the presence of the micro-particles) advantageously increases the area of illumination and flattens the distribution of light over the area to be illuminated.

Figure 5:
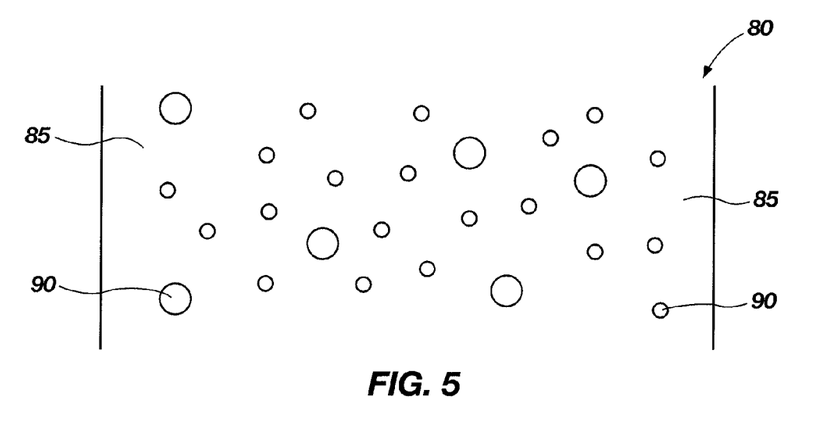
FIG. 5 is a side view of a light diffusing composition according to one embodiment of the present invention.
Figure 6:
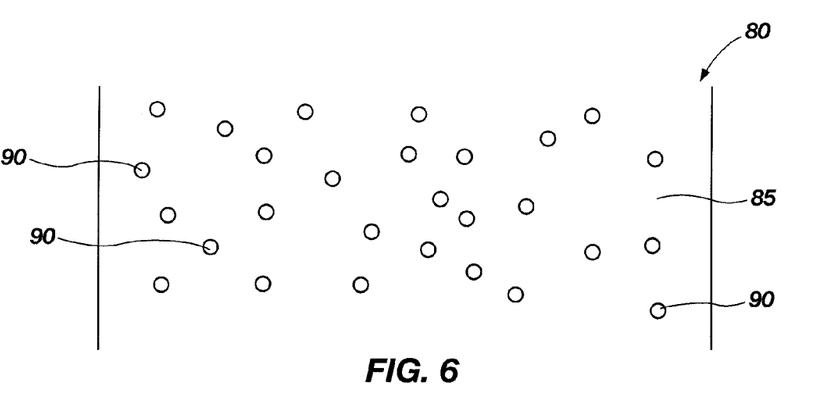
FIG. 6 is a side view of a light diffusing composition according to one embodiment of the present invention.

In one aspect of the present invention, the refractive index of the fluid within the micro particle 90 is less than the refractive index of the matrix 85. In yet another aspect, the absolute value of the difference between the refractive index of the fluid and the refractive index of the matrix 85 is greater than approximately 0.4. In an additional embodiment, the refractive index of the fluid is greater than 1.0. In yet another embodiment, the refractive index of the fluid is less than the refractive index of the hollow micro particle 90. In still another embodiment, the refractive index of the fluid is greater than the refractive index of the matrix 85. In one embodiment, the micro-particles 90 dispersed throughout the matrix 85 have numerous dimensions as illustrated in FIG. 5. In yet another embodiment, the micro-particles 90 dispersed throughout the matrix have substantially equal dimensions. In one embodiment, the micro-particles 90 have a diameter ranging from ten to sixty-five microns (10-65 μm). In yet another embodiment, the micro-particles 90 have a diameter ranging from five to one hundred twenty microns (5-120 μm). However, it is understood that the exact size and shape of the micro particles 90 is tailored as desired for a particular application.

In one embodiment of the present invention, a light diffusing composition is disclosed comprising an opaque matrix comprising a plurality of hollow micro-particles 90, wherein the plurality of hollow micro-particles 90 are dispersed throughout the opaque matrix. A fluid is disposed within the hollow micro-particles 90, wherein the refractive index of the fluid within the hollow micro-particles 90 is different than the refractive index of the opaque matrix. The density of hollow micro-particles 90 dispersed throughout the opaque matrix is sufficient to allow adequate light to pass through the matrix and illuminate a target area. That is, because the opaque matrix decreases the transmission of light through the matrix, the micro-particle density, is such that a substantial number of micro-particles 90 are in contact with one another thereby permitting the transmission of light from micro-particle 90 to micro-particle 90, until the light exits the particular transmission conduit. The micro-particles 90 may be spherical, cubic, amorphous, or some other suitable shape, or a combination of any of these.

In another embodiment of the present invention, the matrix 85 comprises a translucent matrix having a plurality of micro spheres 90 dispersed throughout the translucent matrix, wherein the micro-spheres 90 have a reflective outer surface. In this manner, light is dispersed through the composition 80 based on the reflective properties of the micro-spheres 90 disposed within the translucent matrix 85. In one aspect of the invention, the reflective outer surface of the micro-spheres 90 is coated with a reflective material such as zinc sulfide titanium dioxide, magnesium fluoride, silicon dioxide, etc. In yet another aspect, the outer surface of the micro-spheres is also configured to have granular or rough areas. In this manner, diffuse reflection (e.g., Lambertian reflectance) of light emanating from the light source 62 may be attainable. While use of micro-spheres 90 are referenced in connection with this embodiment, it is understood that numerous shapes (e.g., cubes, prisms, amorphous shapes, etc.) of various materials may be utilized to accomplish the desired light diffusion.

Figure 7:
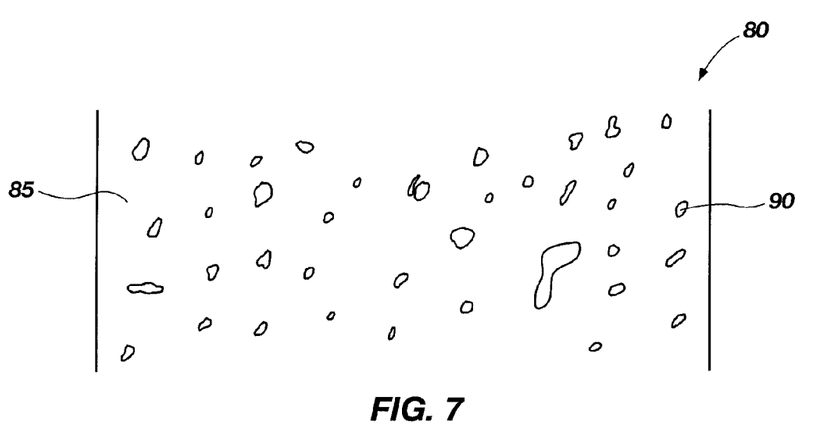
FIG. 7 is a side view of a light diffusing composition according to one embodiment of the present invention.

Referring now to FIG. 7, in yet an additional embodiment of the present invention, the matrix 85 comprises a plurality of fluid-filled compartments 91, wherein a refractive index of the fluid 92 within the compartment 91 is different than a refractive index of the matrix 85. In one embodiment, the light source 62 is oriented in a direction substantially parallel to an image plane of the SSID 55. As noted above, the matrix 85 may comprise a translucent matrix or opaque matrix. The fluid-filled compartments 91 may comprise pockets of air disposed within the matrix 85 or some other fluid (e.g., argon, saline, nitrogen, etc.) as suits a particular application. In one aspect of the invention, the fluid is an inert fluid.

Figure 8:
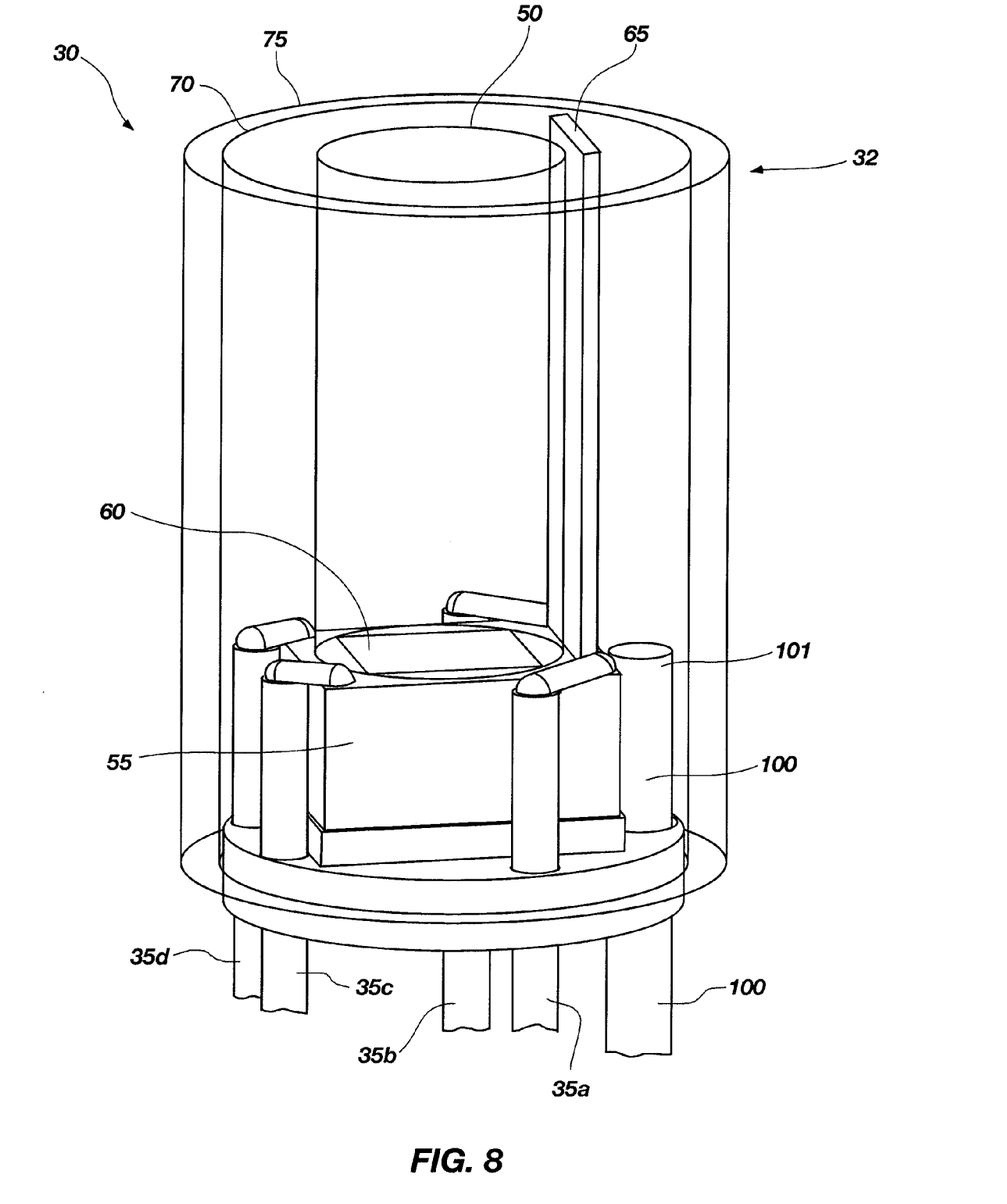
Figure 8A:
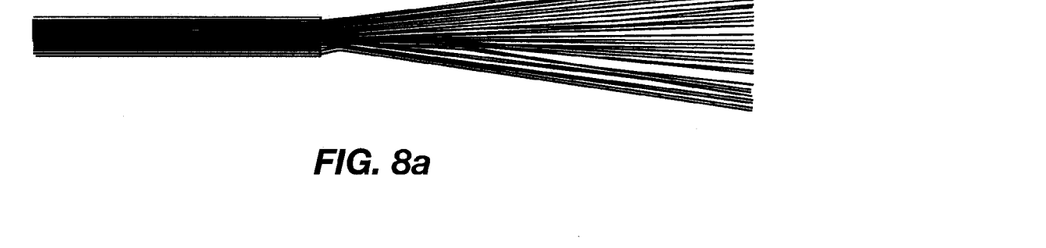
Figure 8B:
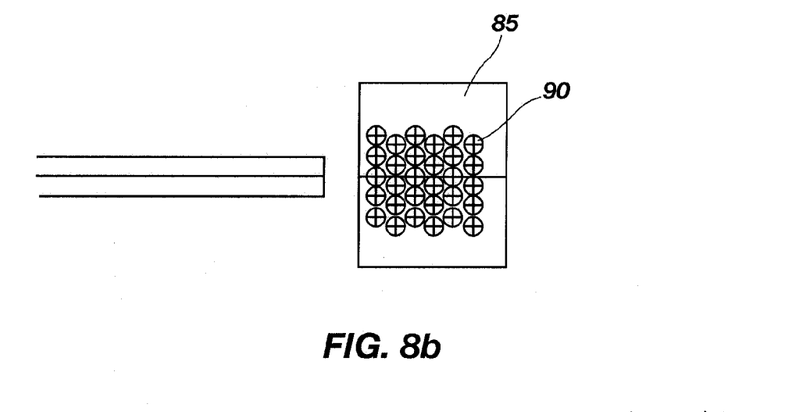
Figure 8C:
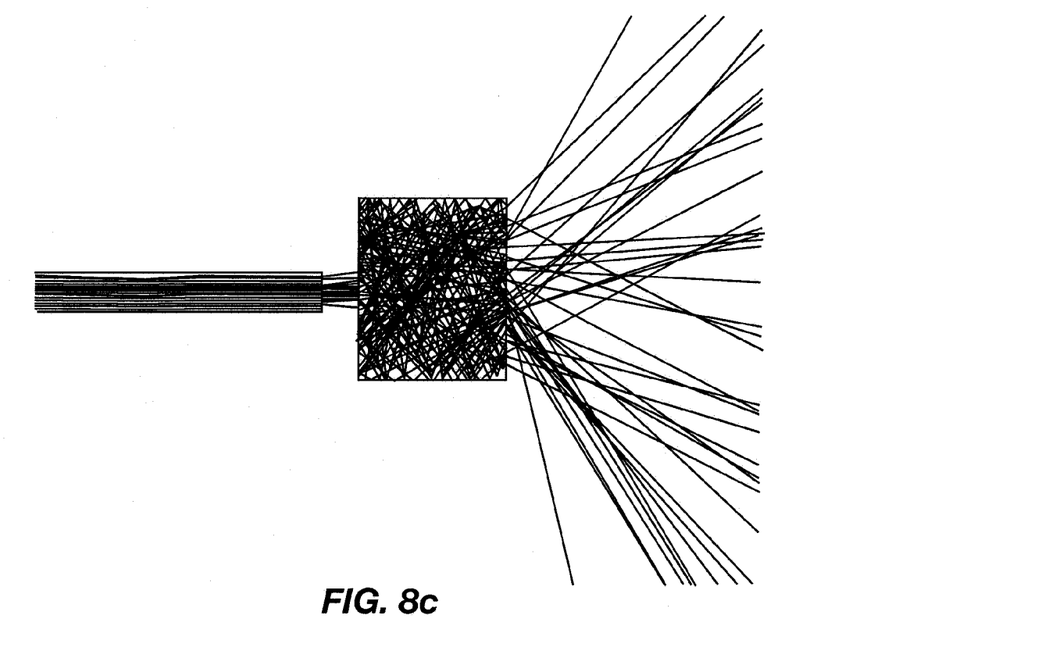

Referring now to FIGS. 8*a* through 8*c*, FIG. 8*a* illustrates how light exits an optical fiber in accordance with one embodiment of the present invention. FIG. 8*b* illustrates a model of an optical fiber and a matrix 85 containing hollow micro-spheres 90 in accordance with one embodiment of the invention. FIG. 8*c* illustrates how the addition of the matrix 85 containing hollow micro-spheres 90 causes light to refract resulting in a more diffuse illumination.

In one embodiment of the present invention, the matrix 85 can be either a structure adhesive or a pressure sensitive adhesive (PSA). The optical properties of a PSA, as described below, allow the PSA to remain stable under high intensity light. Useful PSAs can be, for example, substantially free of unreacted monomers and oligomers and/or photo initiators, and substantially non-shrinking. The PSA materials can be substantially free of UV-absorbing chromophores such as extended aromatic structures or conjugated double bonds. The Pressure-Sensitive-Tape Council has defined pressure sensitive adhesives as material with the following properties: (a) aggressive and permanent tack, (b) adherence with no more than finger pressure, (c) sufficient ability to hold onto an adherand, (d) sufficient cohesive strength, and (e) requires no activation by an energy source. PSAs are normally tacky at assembly temperatures, which is typically room temperature or greater (i.e., about 20 degrees Celsius to about 30 degrees Celsius or greater). Materials that have been found to function well as PSAs are polymers designed and formulated to exhibit the requisite viscoelastic properties resulting in the desired balance of tack, peel adhesion, and shear holding power at the assembly temperature. The most commonly used polymers for preparing PSAs are natural rubber-, synthetic rubber- (e.g., styrene butadiene copolymers (SBR) and styrene/isoprene/styrene (SIS) block copolymers), silicone estomer-, polyalpha- olephfin-, and various (meth) acrylate- (e.g., acrylate and methacrylate) based polymers.

A structural adhesive is a material used to bond high strength materials, such as wood, composites, plastics, glass, or metal, so that the practical adhesive bond strength is in excess of 6.9 MPa (1000 psi) at room temperature. Because of the demands on performance, structural adhesives usually take part in curing and/or cross-linking reactions by external energy source such as UV or heat during assembly leading to the development of final adhesive properties. Structural adhesives may be classified in a number of ways, such as physical form, chemical compositions, and curing conditions of the adhesives. Examples of structural adhesives contemplated herein are phenolic, epoxy, acrylic, urethane, polyimide and bis-maleimide. It is understood herein that the matrix 85 referenced herein is not limited to a pressure sensitive adhesive or a structural adhesive. However, the matrix 85 may comprise a combination of different adhesives or may comprise some other suitable material or combination of suitable materials with the desired optical characteristics for a particular application.

Figure 9:
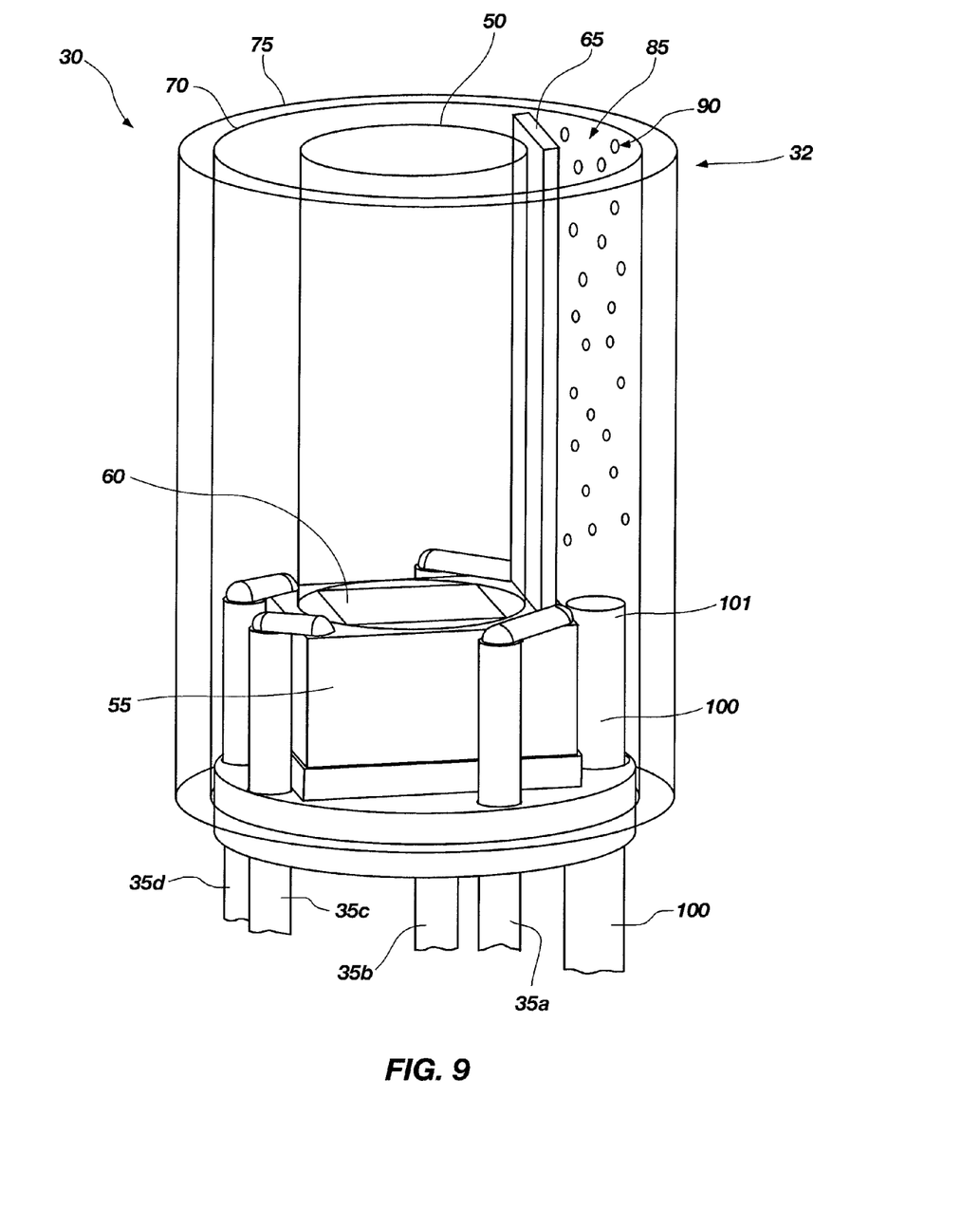
FIG. 9 is a perspective view of an imaging structure according to one embodiment of the present invention.

With reference now to FIGS. 5 through 9, in one embodiment of the present invention a light source 100 is disposed within an aperture of the planar support member 40 to provide light for imaging. While much of the structure of embodiments illustrated in FIGS. 9 and 10 are similar to those illustrated in FIGS. 3 and 4, some similar call-out numbers are referenced herein. In one aspect, a distal end 101 of the light source 100 terminates prior to the distal end 32 of the imaging structure 31. In this embodiment, the light diffusing composition 80 described herein may be disposed within the first sleeve member 70 of the imaging structure 31. In one aspect, the matrix 85 of the light diffusing composition 80 is an adhesive as described herein securing all of the respective components of the imaging structure 31 within the inner volume of the first sleeve member 70. Advantageously, the diffusive properties of the light diffusing composition 80 effectively increase the path length of the light emitted from light source 100 thereby improving image quality as noted herein. In one aspect, an outer portion of the GRIN lens 55 may be coated with an opaque material to minimize light intrusion from light source 100 that has not been reflected from a target area. The opaque material may cover all or part of the outer portion of the GRIN lens.

Referring generally to FIGS. 3 through 7, in an additional embodiment of the present invention, a method of improving the image clarity of a miniature imaging device is disclosed comprising providing a SSID 55 operatively coupled to a lens system 50 (e.g., a GRIN lens or some other suitable lens system) and providing a light source 62 configured to propagate light near the lens system 50. The method further comprises propagating light through a translucent matrix 85 and onto a target surface, the translucent matrix 85 comprising a plurality of fluid-filled compartments 91. A refractive index of the fluid in the compartments 91 is different than a refractive index of the translucent matrix 85. The method further comprises receiving light reflected from the target surface through the lens system 50 and onto the SSID 55.

In another aspect of the invention, the refractive index of the fluid is less than the refractive index of the translucent matrix 85. In yet another aspect of the invention, the absolute value of the difference between the refractive index of the fluid and the refractive index of the translucent matrix 85 is greater than approximately 0.4. In one embodiment, the refractive index of the fluid is greater than the refractive index of the translucent matrix 85. Fluid within the compartments 91 may comprise air or any other fluid (e.g., saline, argon, nitrogen, etc.) suitable for the desired application. As noted in more detail above, in one embodiment of the present invention, the translucent matrix 85 consists of a pressure sensitive adhesive or structural adhesive. The translucent matrix 85 may also comprise some other suitable material with the desired optical characteristics that, when used in conjunction with the fluid-filled compartments 91, creates the desired diffusive effect.

In accordance with one embodiment of the present invention, the matrix may comprise a plurality of compartments that are substantially free of any fluid thereby creating at least a partial vacuum within the compartment. That is, the pressure within the compartment is less than atmospheric pressure and in some instances is substantially less than (i.e., 100 kPa to 3 kPa) atmospheric pressure.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A light diffusing composition disposed within a medical device comprising:
    a light source operatively coupled to the medical device;
    a solid translucent matrix operatively coupled to the light source and disposed at a distal end of the medical device, the matrix comprising a plurality of hollow micro-particles, the plurality of hollow micro-particles being dispersed throughout the translucent matrix and being substantially stationary within the matrix; and
    a fluid disposed within the hollow micro-particle;
    wherein, a refractive index of the fluid within the hollow micro-particle is different than a refractive index of the translucent matrix.

2. The light diffusing composition of claim 1, wherein the refractive index of the fluid is less than the refractive index of the translucent matrix.

3. The light diffusing composition of claim 1, wherein the absolute value of the difference between the refractive index of the fluid and the refractive index of the translucent matrix is greater than approximately 0.4.

4. The light diffusing composition of claim 1, wherein the refractive index of the fluid is greater than 1.0.

5. The light diffusing composition of claim 1, wherein the refractive index of the fluid is less than the refractive index of the hollow micro-particle.

6. The light diffusing composition of claim 1, wherein the fluid is inert and wherein the refractive index of the fluid is greater than the refractive index of the translucent matrix.

7. A light diffusing composition disposed within a medical device, comprising:
    a light source operatively coupled to the medical device:
    an opaque matrix comprising a plurality of hollow translucent micro-particles, the plurality of hollow translucent micro-particles being dispersed throughout the opaque matrix to form a continuous pathway of light through the opaque matrix; and
    a fluid disposed within the hollow translucent micro-particle;
    wherein, a refractive index of the fluid within the hollow translucent micro-particle is different than a refractive index of the micro-particle's shell.

8. A medical imaging device, comprising:
    a light source operatively coupled to the medical imaging device;
    a solid state imaging device operatively coupled to a lens system;
    wherein the light source is configured to propagate light near the lens system; and
    a solid matrix disposed on a distal end of the light source, the matrix comprising a plurality of fluid-filled compartments, wherein a refractive index of the fluid is different than a refractive index of the matrix.

9. The medical imaging device of claim 8, wherein the light source is oriented in a direction substantially parallel to an image plane of the solid state imaging device.

10. The medical imaging device of claim 8, wherein the matrix is a translucent matrix.

11. The medical imaging device of claim 8 wherein the matrix is an opaque matrix.

12. The medical imaging device of claim 10, wherein the absolute value of the difference between the refractive index of the fluid and the refractive index of the translucent matrix is greater than approximately 0.4.

13. The medical device of claim 8, wherein the matrix occludes the distal end of the elongated hollow member.

14. A medical imaging device, comprising:
    a light source operatively coupled to the medical imaging device;
    a solid state imaging device operatively coupled to a lens system;
    wherein the a light source is configured to propagate light near the lens system; and
    a translucent matrix disposed on a distal end of the light source, the translucent matrix comprising a plurality of micro-spheres dispersed throughout the translucent matrix, the micro spheres having a reflective outer surface.

15. A method of improving the image clarity of a miniature imaging device, comprising:
    (a) providing a solid state imaging device operatively coupled to a lens system and disposed on a distal end of an elongate member adapted to be placed within a cavity of a body;
    (b) providing a light source configured to propagate light near the lens system, wherein the light source is operatively coupled to the medical imaging device;
    (c) propagating light through a translucent matrix and onto a target surface, the translucent matrix comprising a plurality of fluid-filled compartments, wherein a refractive index of the fluid is different than a refractive index of the translucent matrix; and
    (d) receiving light reflected from the target surface through the lens system and onto the solid state imaging device.

16. The method of claim 15, wherein the refractive index of the fluid is less than the refractive index of the translucent matrix.

17. The method of claim 15, wherein the absolute value of the difference between the refractive index of the fluid and the refractive index of the translucent matrix is greater than approximately 0.4.

18. The method of claim 15, wherein the refractive index of the fluid is greater than the refractive index of the translucent matrix.

19. The method of claim 18, wherein the fluid is air.

20. The method of claim 15, wherein the translucent matrix consists of a pressure sensitive adhesive or structural adhesive.

21. A medical imaging device, comprising:
    a light source operatively coupled to the medical imaging device;
    a solid state imaging device operatively coupled to a lens system;

wherein the light source is configured to propagate light near the lens system; and a matrix disposed on a distal end of the light source, the matrix comprising a plurality of hollow compartments.

22. The medical imaging device of claim 21, wherein the pressure of the hollow compartment is less than atmospheric pressure.

* * * * *